(12) United States Patent
Krabichler et al.

(10) Patent No.: US 9,107,836 B2
(45) Date of Patent: Aug. 18, 2015

(54) FORMULATION

(75) Inventors: Michaela Krabichler, Muttenz (CH); Bernard Meyer, Dietwiller (FR); Carsten Winzenburg, Inzlingen (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 172 days.

(21) Appl. No.: 13/288,082

(22) Filed: Nov. 3, 2011

(65) Prior Publication Data

US 2012/0115946 A1    May 10, 2012

(30) Foreign Application Priority Data

Nov. 4, 2010 (EP) .................................. 10190045

(51) Int. Cl.
*A61K 9/20* (2006.01)
*A61K 31/265* (2006.01)

(52) U.S. Cl.
CPC .............. *A61K 9/2054* (2013.01); *A61K 31/265* (2013.01)

(58) Field of Classification Search
USPC ........................................................ 424/464
See application file for complete search history.

(56) References Cited

U.S. PATENT DOCUMENTS

| 2004/0197398 A1 | 10/2004 | Friesen et al. |
| 2008/0138428 A1 | 6/2008 | Ray et al. |

FOREIGN PATENT DOCUMENTS

| EP | 1020439 | 7/2000 |
| WO | 2004082593 | 9/2004 |
| WO | 2004082675 | 9/2004 |
| WO | 2005/011634 | 2/2005 |
| WO | 2007/051714 | 5/2007 |
| WO | 2008/074677 | 6/2008 |
| WO | 2010/066593 | 6/2010 |
| WO | 2011/000793 | 1/2011 |

OTHER PUBLICATIONS

Stein (Safety and tolerability of dalcetrapib:results from a 48 week trial, European Heart Journal vol. 31, pp. 480-488, Jan. 22, 2010).*
Buhler (Polyvinylpyrrolidone Excipients for Pharmaceuticals, §3.4.2.6, p. 160, 2005).*
Kobayashi et al., Atherosclerosis 162:131-135 ( 2002).
De Grooth et al., Circulation 105:2159-2165 ( 2002).
Shinkai et al., J. Med. Chem. 43:3566-3572 ( 2000).
(International Search Report for PCT/EP2011/069087 Dec. 7, 2011).
Okamoto et al., Nature 406:203-207 (Jul. 2000).
The New Zealand Office Action, issued on Feb. 19, 2014, in the corresponding New Zealand application No. 609529.
The English translation of the Japanese Office Action, issued on Jul. 29, 2014, in the corresponding Japanese application No. 2013-537093.
Handbook of Pharmaceutical Excepients Fifth Edition, YaKuji Nippo Ltd, Feb. 28, 2007, p. 276-282.
The Japanese Pharmaceutical Excipients Dictionary, 2007, YaKuji Nippo Ltd., 1st edition, p. 93, 1086.
The English translation of the Korean Office Action, issued on Nov. 4, 2014, in the corresponding Korean application No. 2013-7014214.

\* cited by examiner

*Primary Examiner* — Adam C Milligan

(57) ABSTRACT

The present invention relates to a hygroscopic matrix based formulation, a process for the preparation thereof and its use in the treatment of diseases.

3 Claims, 3 Drawing Sheets

FORMULATION

PRIORITY TO RELATED APPLICATION(S)

This application claims the benefit of European Patent Application No. 10190045.4, filed Nov. 4, 2010, which is hereby incorporated by reference in its entirety.

BACKGROUND OF THE INVENTION

Active pharmaceutical ingredients showing an ester, amide or thioester functionality are often sensitive to moisture and frequently show chemical incompatibility with a wide range of commonly used pharmaceutical excipients, thus typical formulation approaches such as lipid based drug delivery systems can not be considered. Incorporating the drug substance into a hygroscopic polymer matrix can be critical due to chemical as well as physical stability. The sorption of moisture by excipients in solid dosage forms can lead to considerable stability problems when the contained active pharmaceutical is instable in water due to the presence of a hydrolysis sensitive functional group. Though theoretically hygroscopic polymers are capable to bind moisture in the formulation, thus protecting the active pharmaceutical ingredient from hydrolysis, a fairly high amount of polymer is needed to achieve this what usually leads to capping or cracking of the immediate-release tablet formulation. Thus, it is usually imperative to prevent moisture sorption during storage by both, a suitable formulation and primary packaging.

SUMMARY OF THE INVENTION

The present invention relates to a hygroscopic matrix based formulation, a process for the preparation thereof and its use in the treatment of diseases.

DETAILED DESCRIPTION OF THE INVENTION

Figure 1:
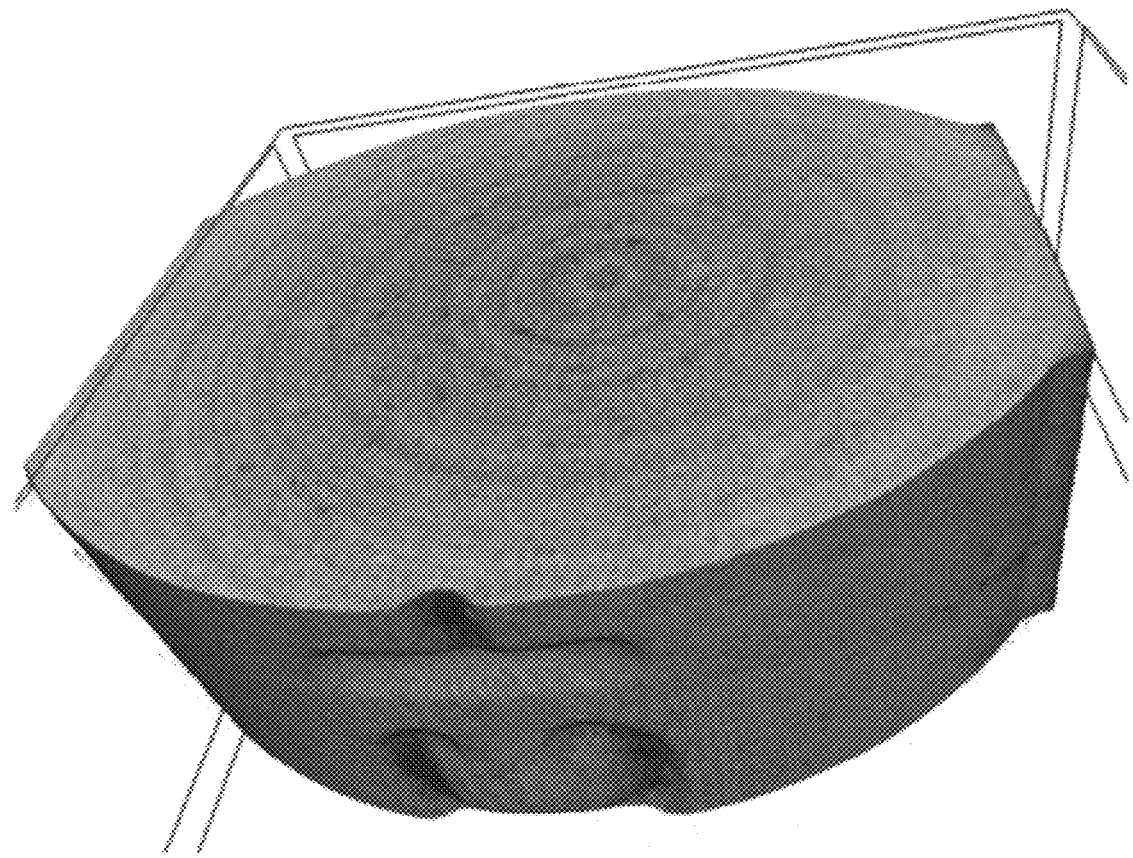
FIG. 1 is a 3D reconstruction of all X-ray slices of a tablet produced according to example 1.

Unless otherwise stated, the following terms used in the specification and claims have the meanings given below:

The term "bulk density" refers to a density measurement of a loose, uncompacted substance, wherein the volume of the substance includes the air trapped between particles. The bulk density is measured in a graduated cylinder according to the European Pharmacopeia.

The term "diluent" refers to an excipient which fills out the size of a tablet or capsule, making it practical to produce and convenient for the consumer to use. Suitable diluents include e.g. pharmaceutically acceptable fillers, such as microcrystalline cellulose (e.g. Avicel®), crospovidone micronized, cellulose powder, lactose spray-dried, lactose anhydrous, lactose monohydrate, dibasic calcium phosphate, sugars, sugar alcohols, corn starch, starch, pregelatinized starch, colloidal silicon dioxide, polysaccharides, and mixtures thereof.

The term "hydrophobic" means insoluble in water, not readily absorbing moisture, or being adversely affected by water; either incompatible with water or having little affinity for it. In other words the hydrophobic drug or compound would not spontaneously disperse in water. Specifically hydrophobic means log P>3. The log P is measured or in the absence of experimental data calculated as clog P according to the model developed by Moriguchi (S. Moriguchi, S. Hirono, I. Nakagome, H. Hirano, (1994). "Comparison of reliability of log P values for drugs calculated by several methods" *Chem Pharm Bull* 1994, 42:976-978).

The term "hygroscopic polymeric excipient(s)" means polymeric excipient(s) which take(s) up moisture for example by absorption or adsorption even at relative humidity as low as 50%, at room temperature (e.g. about 25° C.). The moisture uptake is measured e.g. by dynamic vapor sorption at room temperature. As an example the hygroscopicity can be measured in accordance with the method disclosed in the European Pharmacopoeia—6th Edition (2008), Chapter 5.11. The dynamic vapor sorption technique measures the change in mass which is produced by varying the vapor concentration surrounding the product. Suitable "hygroscopic polymeric excipients" are hydroxypropyl methylcellulose, hydroxypropyl cellulose, low-substituted hydroxypropyl cellulose, hydroxyethylmethyl cellulose, carboxypolymethylene, methylcellulose, ethylcellulose, hydroxyethyl cellulose, celluloseacetate, polyvinylpyrrolidone crosslinked polyvinylpyrrolidone, micronized crosslinked polyvinylpyrrolidone, carboxymethylcellulose sodium, carboxymethylcellulose calcium, crosslinked carboxymethylcellulose, microcrystalline cellulose, silicified microcrystalline cellulose, cellulose powder, carboxymethyl starch, starch, pregelatinized starch or mixture thereof. In particular "hygroscopic polymeric excipients" refer to hydroxypropyl methylcellulose, carboxymethylcellulose sodium, microcrystalline cellulose and micronized crosslinked polyvinylpyrrolidone. Examples of "water insoluble hygroscopic polymers" at room temperature (e.g. about 25° C.) include low-substituted hydroxypropyl cellulose, carboxypolymethylene, ethylcellulose, celluloseacetate, crosslinked polyvinylpyrrolidone, micronized crosslinked polyvinylpyrrolidone, carboxymethylcellulose calcium, microcrystalline cellulose, silicified microcrystalline cellulose, cellulose powder, and starch.

The term "Super-disintegrant" refers to disintegrants that very rapidly expand upon contact with water. Generally speaking, superdisintegrants are disintegration agents which can be used in a fractional amount of normal disintegrants to obtain the same effect. Examples of superdisintegrants include cross-linked carboxymethyl cellulose sodium (a.k.a. croscarmellose sodium), sodium starch glycolate, and cross-linked polyvinyl pyrollidone (a.k.a. crospovidone). Croscarmellose sodium is commercially available from FMC Corp. under the trade name Ac-Di-Sol® and from Avebe Corp. under the trade name Primellose®®. Sodium starch glycolate is commercially available from Penwest Pharmaceuticals Co. under the trade name Explotab® and from Avebe Corp, under the trade name Primojel®. Crospovidone is commercially available from BASF Corp. under the trade name Kollidon® CL and from International Specialty Chemicals Corp. under the trade name Polyplasdone®, Croscarmellose is also commercially available from Mingtai Chemical Co. Ltd under the trade name DISOLCEL® and from J. Rettenmaier & Söhne GmbH+Co (JRS) under the trade name Vivasol®. The most preferred superdisintegrants are croscarmellose sodium and crospovidone.

The term "water instable" means the presence of a hydrolysis sensitive functional group like an ester, amide or thioester.

The term "waxy consistency" means that the glass transition temperature (Tg) is lower than 25° C.

The term "halo" means chloro, bromo, iodo or fluoro.

"Aryl" means a monovalent monocyclic or bicyclic aromatic hydrocarbon moiety. More specifically the term aryl includes, but is not limited to, phenyl, 1-naphthyl, 2-naphthyl, and the like, each of which can be substituted or unsubstituted.

"$(C_2$-$C_6)$alkenyl" refers to a straight- or branched-chain of 2 to 6 carbon atoms. In particular embodiments the $(C_2$-$C_6)$ alkenyl has 2 to 4 carbon atoms, with at least one double bond. Examples of alkenyl include ethenyl, propenyl, prop-2-enyl, isopropenyl, n-butenyl, i-butenyl, and t-butenyl.

"$(C_1$-$C_8)$alkyl" refers to a branched or straight hydrocarbon chain of one to eight carbon atoms. Examples include methyl, ethyl, n-propyl, isopropyl, n-butyl, isobutyl, sec-butyl, t-butyl, pentyl, hexyl and heptyl. A $(C_1$-$C_6)$alkyl is preferred.

"Halo-$(C_1$-$C_8)$alkyl" refers to an alkyl, as defined above, substituted with one or more halogen atoms. In particular embodiments the halo-$(C_1$-$C_8)$alkyl is substituted with one to three halogen atoms. A more preferred halo-$(C_1$-$C_8)$alkyl is the chloro- or fluoro-$(C_1$-$C_8)$alkyl.

"Aralkyl" refers to a moiety of the formula —$R^{bc}$—$R^{bd}$ where $R^{bd}$ is aryl and $R^{bc}$ is $(C_1$-$C_6)$alkylene as defined herein.

"$(C_1$-$C_6)$alkoxy" means a moiety of the formula —$OR^{ab}$, wherein $R^{ab}$ is an $(C_1$-$C_6)$alkyl moiety as defined herein. Examples of alkoxy moieties include, but are not limited to, methoxy, ethoxy, isopropoxy, and the like.

"$(C_3$-$C_8)$cycloalkyl" refers to a single saturated carbocyclic ring. Examples include cyclopropyl, cyclobutyl, cyclopentyl, cyclohexyl, cycloheptyl and cyclooctyl.

"$C_3$-$C_8$cycloalkyl$C_1$-$C_8$alkyl" refers to an alkyl, as defined above, substituted by one $(C_3$-$C_8)$cycloalkyl as defined above.

"Acyl" means a group of the formula —C(O)—$R^{ag}$, —C(O)—$OR^{ag}$, —C(O)—OC(O)$R^{ag}$ or —C(O)—$NR^{ag}R^{ah}$ wherein $R^{ag}$ is hydrogen, $(C_1$-$C_6)$alkyl, halo$(C_1$-$C_6)$alkyl or amino as defined herein, and $R^{ah}$ is hydrogen or $(C_1$-$C_6)$alkyl as defined herein.

Unless otherwise stated all percentages are given in weight percent of the total weight of the composition.

In a first aspect, the present invention provides a pharmaceutical composition comprising a hydrophobic, water instable compound with a waxy consistency and a super-disintegrant.

In a second aspect, the present invention provides a pharmaceutical composition comprising a hydrophobic, water instable compound with a waxy consistency, a super-disintegrant and at least two diluents with a bulk density lower than 800 g/L.

The invention also provides a method for treating or preventing a cardiovascular disorder in a mammal by administering to a mammal in need of such treatment a therapeutically effective amount of the pharmaceutical composition provided by the invention.

The invention further provides a formulation for treating or preventing a cardiovascular disorder. A composition according to the present invention for the use in the treatment or prevention of cardiovascular disorder is also part of the invention.

The hygroscopic matrix based formulation is useful to chemically stabilize a hydrophobic and hydrolysis sensitive compound with a waxy consistency, e.g. a cholesteryl ester transfer protein inhibitor (CETP inhibitor), and to stabilize the physical properties of a tablet comprising said formulation.

The manufacturing of the composition according to the present invention shows surprisingly better flowability than past compositions comprising a hydrophobic, water instable compound with a waxy consistency. For instance, the composition according to the present invention does not demonstrate extreme funnel flow.

In a particular embodiment, the hydrophobic, water instable compound with a waxy consistency is a CETP inhibitor thioester derivative, such as those disclosed in EP 1020439 A1. Specific thioester compounds include the compounds of formula I:

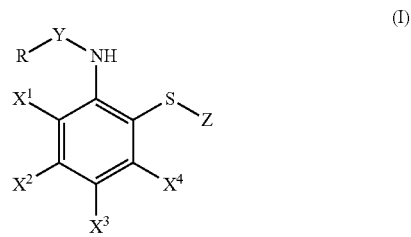

(I)

wherein:
R is $C_1$-$C_8$alkyl, $C_2$-$C_6$alkenyl, halo$C_1$-$C_8$alkyl, $C_3$-$C_8$cycloalkyl, $C_3$-$C_8$cycloalkyl$C_1$-$C_8$alkyl, aryl, aralkyl or a 5- or 6-membered heterocyclic group having 1 to 3 nitrogen, oxygen or sulfur atoms, $X^1$, $X^2$, $X^3$ and $X^4$ independently are hydrogen, halogen, $C_1$-$C_8$alkyl, halo$C_1$-$C_8$alkyl, $C_1$-$C_6$alkoxy, cyano, nitro, acyl or aryl, Y is —CO— or —$SO_2$; and Z is hydrogen, $C_1$-$C_8$alkyl, $C_3$-$C_8$cycloalkyl or $C_3$-$C_8$cycloalkyl$C_1$-$C_8$alkyl.

In a more preferred embodiment of the present invention, the CETP inhibitor thioester derivative is thioisobutyric acid S-(2-{[1-(2-ethyl-butyl)-cyclohexanecarbonyl]-amino}-phenyl) ester, also know as S-[2-([[1-(2-ethylbutyl)-cyclohexyl]-carbonyl]amino)phenyl]2-methylpropanethioate (dalcetrapib) shown structurally as the compound of formula I':

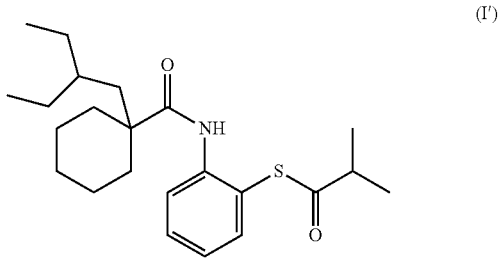 [SMILES: CCC(CC)CC1(C(=O)Nc2ccccc2SC(=O)C(C)C)CCCCC1]

(I')

S-[2-([[1-(2-ethylbutyl)cyclohexyl]carbonyl]amino)phenyl] 2-methylpropanethioate has been shown to be an inhibitor of CETP activity in humans (de Grooth et al., Circulation, 105, 2159-2165 (2002)) and rabbits (Shinkai et al., J. Med. Chem., 43, 3566-3572 (2000); Kobayashi et al., Atherosclerosis, 162, 131-135 (2002); and Okamoto et al., Nature, 406 (13), 203-207 (2000)). S-[2-([[1-(2-ethylbutyl)cyclohexyl] carbonyl]amino)phenyl] 2-methylpropanethioate has been shown to increase plasma HDL cholesterol in humans (de Grooth et al., supra) and in rabbits (Shinkai et al., supra; Kobayashi et al., supra; Okamoto et al., supra). Moreover, S-[2-([[1-(2-ethylbutyl)cyclohexyl]carbonyl]amino)phenyl] 2-methylpropanethioate has been shown to decrease LDL cholesterol in humans (de Grooth et al., supra) and rabbits (Okamoto et al., supra). Additionally, S-[2-([[1-(2-ethylbutyl)cyclohexyl]carbonyl]amino)phenyl] 2-methylpropanethioate inhibits the progression of atherosclerosis in rabbits (Okamoto et al., supra). S-[2-([[1-(2-ethylbutyl)cyclohexyl]carbonyl]amino)phenyl] 2-methylpropanethioate, as well as methods of making and using the compound, are described in EP patent EP1020439, Shinkai et al., J. Med. Chem. 43:3566-3572 (2000) or WO 2007/051714, WO 2008/074677 or WO2011/000793.

In a preferred embodiment the CETP inhibitor thioester derivative (e.g. compound of formula I or I') is a solid in crystalline or amorphous form, more preferably in crystalline form. In a particular embodiment S-[2-([[1-(2-ethylbutyl)-cyclohexyl]-carbonyl]amino)phenyl]2-methylpropanethioate is in crystalline form A.

Form A is characterized by an X-ray powder diffraction pattern having peaks at about 7.9°, 8.5°, 11.7°, 12.7°, 17.1°, 18.0°, 18.5°, 20.2°, 22.1°, 24.7°±0.2°, particularly by an XRPD peaks observed at an angle of diffraction 2 Theta of 7.9°, 11.7°, 17.1°, 18.5° (±0.2°).

The pharmaceutical composition can be used to treat or prevent a cardiovascular disorder, including, but not limited to, atherosclerosis, peripheral vascular disease, dyslipidemia (e.g., hyperlipidimia), hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, hypertension, cardiovascular disease, coronary heart disease, coronary artery disease, hyperlipidoproteinemia, vascular complications of diabetes, obesity or endotoxemia in a mammal, especially a human (i.e., a male or female human).

Accordingly, the invention provides a method for the treatment or prophylaxis of a cardiovascular disorder in a mammal, which method comprises administering to a mammal (preferably a mammal in need thereof) a therapeutically effective amount of the pharmaceutical composition. The mammal preferably is a human (i.e., a male or female human). The human can be of any race (e.g., Caucasian or Oriental). The cardiovascular disorder preferably is selected from the group consisting of atherosclerosis, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, hypertension, and vascular complications of diabetes, obesity or endotoxemia in a mammal. More preferably, the cardiovascular disorder is selected from the group consisting of cardiovascular disease, coronary heart disease, coronary artery disease, hypoalphalipoproteinemia, hyperbetalipoproteinemia, hypercholesterolemia, hyperlipidemia, atherosclerosis, hypertension, hypertriglyceridemia, hyperlipidoproteinemia, peripheral vascular disease, angina, ischemia, and myocardial infarction.

In certain embodiments of the present invention, the pharmaceutical composition comprises: 10% to 69% by weight, preferably 40% to 60% by weight, more preferably 48% to 55% by weight of a hydrophobic, water instable compound with a waxy consistency.

In certain embodiments of the present invention, the pharmaceutical composition comprises: 1% to 10% by weight, preferably 5% to 10% by weight, more preferably 4% to 8% by weight of a super-disintegrant.

In certain embodiments of the present invention, the pharmaceutical composition comprises 30% to 70% by weight, preferably 30% to 60% by weight, more preferably 40% to 50% by weight of at least two diluents with a bulk density lower than 800 g/L.

In a particular embodiment, the present invention provides a pharmaceutical composition comprising:

10% to 69% by weight, preferably 40% to 60% by weight, more preferably 48% to 55% by weight of a hydrophobic, water instable compound with a waxy consistency 1% to 10% by weight, preferably 5% to 10% by weight, more preferably 4% to 8% by weight of a super-disintegrant, and 30% to 70% weight, preferably 30% to 60% by weight, more preferably 40% to 50% by weight of at least two diluents with a bulk density lower than 800 g/L.

In certain embodiments of the present invention as defined herein, the super-disintegrant is a hygroscopic polymeric excipient. In particular the hygroscopic polymeric excipient as superdisintegrant is croscarmellose sodium.

In a particular embodiment, the present invention provides a composition comprising: S-[2-([[1-(2-ethylbutyl)-cyclohexyl]-carbonyl]amino)phenyl]2-methylpropanethioate, and croscarmellose sodium.

In certain embodiments of the present invention as defined herein, the composition further comprises at least one additional hygroscopic polymeric excipient.

In certain embodiments of the present invention as defined herein, the composition further comprises at least two hygroscopic polymeric excipients.

In certain embodiments of the present invention as defined herein, the composition further comprises at least three hygroscopic polymeric excipients of which two are diluents with a bulk density lower than 800 g/L.

In certain embodiments of the present invention as defined herein, the composition comprises 10% to 69% by weight of S-[2-([[1-(2-ethylbutyl)-cyclohexyl]-carbonyl]amino)phenyl]2-methylpropanethioate.

In certain embodiments of the present invention, the pharmaceutical composition comprises: 10% to 69% by weight, preferably 40% to 60% by weight, more preferably 48% to 55% by weight of S-[2-([[1-(2-ethylbutyl)-cyclohexyl]-carbonyl]amino)phenyl]2-methylpropanethioate.

In certain embodiments of the present invention as defined herein, the composition comprises 1% to 10% by weight, preferably 5% to 10% by weight, more preferably 5% to 8% by weight of croscarmellose sodium. More particularly, in a certain embodiment, the composition comprises 5% to 7% by weight of croscarmellose sodium.

In certain embodiments of the present invention as defined herein, the composition comprises at least 30% by weight of the hygroscopic polymeric excipients, in particular 44% to 50% by weight, more particularly 46% to 48% by weight, wherein the hygroscopic polymeric excipients are hydroxypropylmethyl cellulose, croscarmellose sodium, microcrystalline cellulose and micronized crosslinked polyvinylpyrrolidone.

In certain embodiments of the present invention as defined herein, the composition comprises at least 30% by weight of the hygroscopic polymeric excipients, preferably 34% to 44% by weight, more preferably 40% to 44% by weight.

In certain embodiments of the present invention as defined herein, the composition comprises at least 30% by weight of the additional hygroscopic polymeric excipients, preferably 34% to 44% by weight, more preferably 40% to 44% by weight.

In a particular embodiment, the present invention provides a pharmaceutical composition comprising:

10% to 69% by weight, preferably 40% to 60% by weight, more preferably 48% to 55% by weight of S-[2-([[1-(2-ethylbutyl)-cyclohexyl]-carbonyl]amino)phenyl]2-methylpropanethioate;

1% to 10% by weight, preferably 5% to 10% by weight, more preferably 4% to 8% by weight of croscarmellose sodium, and 30% to 90% by weight, preferably 34% to 44% by weight, more preferably 40% to 44% by weight of the hygroscopic polymeric excipients;

wherein the hygroscopic polymeric excipients are selected from hydroxypropylmethyl cellulose, microcrystalline cellulose and micronized crosslinked polyvinylpyrrolidone.

In certain embodiments of the present invention as defined herein, the composition comprises:
a) 48% to 55% by weight of S-[2-([[1-(2-ethylbutyl)-cyclohexyl]-carbonyl]amino)phenyl]2-methylpropanethioate;
b) 4% to 8% by weight, of croscarmellose sodium;
c) 32% to 41% by weight of water insoluble hygroscopic polymer; and
d) 4% to 5% by weight of water soluble hygroscopic polymer.

In certain embodiments of the present invention as defined herein, wherein the hygroscopic polymeric excipients are selected from hydroxypropylmethyl cellulose, hydroxypropyl cellulose, low-substituted hydroxypropyl cellulose, hydroxyethylmethyl cellulose, carboxypolymethylene, methylcellulose, ethylcellulose, hydroxyethyl cellulose, celluloseacetate, polyvinylpyrrolidone, crosslinked polyvinylpyrrolidone, micronized crosslinked polyvinylpyrrolidone, carboxymethylcellulose calcium, crosslinked carboxymethylcellulose, microcrystalline cellulose, silicified microcrystalline cellulose, cellulose powder, carboxymethyl starch, starch and pregelatinized starch.

In certain embodiments of the present invention as defined herein, the hygroscopic polymeric excipients are hydroxypropylmethyl cellulose, microcrystalline cellulose and micronized crosslinked polyvinylpyrrolidone.

In another embodiment, the invention provides a process for the preparation of the composition comprising the following steps:
a) mixing and granulating, S-[2-([[1-(2-ethylbutyl)-cyclohexyl]-carbonyl]amino)phenyl]2-methylpropanethioate, crospovidone, microcrystalline cellulose, croscarmellose sodium and hydroxypropyl methylcellulose;
b) spraying up to 0.5% by weight of HPMC in water or in 10%-30% ethanol by weight/70%-90% water by weight, onto the granulates obtained according to step a);
c) drying the granulates; and
d) blending microcrystalline cellulose, colloidal silicon dioxide and sodium stearylfumarate with the dry granulates obtained according to step c).

In certain embodiments of the present invention as defined herein, the two diluents are hygroscopic polymeric excipients. In particular the hygroscopic polymeric excipients as diluents are ethylcellulose, micronized crosslinked polyvinylpyrrolidone, microcrystalline cellulose, silicified microcrystalline cellulose, cellulose powder, starch, and/or pregelatinized starch.

In certain embodiments of the present invention as defined herein, at least two hygroscopic polymeric excipients are present.

In certain embodiments of the present invention as defined herein, the super-disintegrant and at least one of the diluents, or at least two diluents are hygroscopic polymeric excipients. More preferably, at least the super-disintegrant and one of the diluents are hygroscopic polymeric excipients.

In certain embodiments of the present invention as defined herein, the super-disintegrant and the two diluents are hygroscopic polymeric excipients.

In certain embodiments of the present invention as defined herein, there is at least 30% by weight of hygroscopic polymeric excipients, preferably 44% to 50% by weight.

In certain embodiments of the present invention, the super-disintegrant is croscarmellose sodium. In particular, the present invention comprises up to 6% by weight of croscarmellose sodium.

The invention provides a physically stable pharmaceutical composition comprising at least one hydrophobic and water instable cholesteryl ester transfer protein (CETP) inhibitor or a combination thereof embedded in a chemically protective hygroscopic polymer matrix tablet consisting of at least one hygroscopic polymer e.g. hydroxypropylmethyl cellulose (HPMC), hydroxypropyl cellulose (HPC), low-substituted hydroxypropyl cellulose (L-HPC), hydroxyethylmethyl cellulose (HEMC), carboxypolymethylene (Carbomer), methylcellulose (MC), ethylcellulose (EC), hydroxyethyl cellulose (HEC), celluloseacetate, polyvinylpyrrolidone (PVP), crosslinked polyvinylpyrrolidone (Crospovidone), micronized crosslinked polyvinylpyrrolidone (crospovidone micronized), carboxymethylcellulose sodium (croscarmellose sodium, CMC Na), carboxymethylcellulose calcium (croscarmellose calcium, CMC Ca), crosslinked carboxymethylcellulose (Crosslinked CMC), microcrystalline cellulose (MCC), silicified microcrystalline cellulose (silicified MCC), cellulose powder, carboxymethyl starch (sodium starch glycolate), starch (maize starch, potato starch, rice starch, wheat starch, tapioca starch), pregelatinized starch or a combination thereof in an amount of preferably 40% by weight or more per unit.

The invention provides a physically stable pharmaceutical composition comprising at least S-[2-([[1-(2-ethylbutyl)-cyclohexyl]-carbonyl]amino)phenyl]2-methylpropanethioate or a combination thereof embedded in a chemically protective hygroscopic polymer matrix tablet consisting of at least one hygroscopic polymer e.g. hydroxypropylmethyl cellulose (HPMC), hydroxypropyl cellulose (HPC), low-substituted hydroxypropyl cellulose (L-HPC), hydroxyethylmethyl cellulose (HEMC), carboxypolymethylene (Carbomer), methylcellulose (MC), ethylcellulose (EC), hydroxyethyl cellulose (HEC), celluloseacetate, polyvinylpyrrolidone (PVP), crosslinked polyvinylpyrrolidone (Crospovidone), micronized crosslinked polyvinylpyrrolidone (crospovidone micronized), carboxymethylcellulose sodium (croscarmellose sodium, CMC Na), carboxymethylcellulose calcium (croscarmellose calcium, CMC Ca), crosslinked carboxymethylcellulose (Crosslinked CMC), microcrystalline cellulose (MCC), silicified microcrystalline cellulose (silicified MCC), cellulose powder, carboxymethyl starch (sodium starch glycolate), starch (maize starch, potato starch, rice starch, wheat starch, tapioca starch), pregelatinized starch or a combination thereof in an amount of preferably 40% by weight or more per unit.

In particular, the present invention provides a physically stable pharmaceutical composition comprising at least one hydrophobic and water instable cholesteryl ester transfer protein (CETP) inhibitor embedded in a chemically protective hygroscopic polymer matrix tablet consisting of hydroxypropylmethyl cellulose, carboxymethylcellulose sodium, microcrystalline cellulose and micronized crosslinked polyvinylpyrrolidone.

In particular, the present invention provides a physically stable pharmaceutical composition comprising at least S-[2-([[1-(2-ethylbutyl)-cyclohexyl]-carbonyl]amino)phenyl]2-methylpropanethioate embedded in a chemically protective hygroscopic polymer matrix tablet consisting of hydroxypropylmethyl cellulose, carboxymethylcellulose sodium, microcrystalline cellulose and micronized crosslinked polyvinylpyrrolidone.

The invention provides a physically stable pharmaceutical composition comprising at least S-[2-([[1-(2-ethylbutyl)-cyclohexyl]-carbonyl]amino)phenyl]2-methylpropanethioate embedded in a chemically protective hygroscopic polymer matrix tablet consisting of hydroxypropylmethyl cellulose, carboxymethylcellulose sodium, microcrystalline cellulose and micronized crosslinked polyvinylpyrrolidone in an amount of preferably 40% by weight or more per unit.

Usually bringing a moisture sensitive active pharmaceutical ingredient in contact with a high amount of hygroscopic polymers such as HPMC, HPC, PVP, Crospovidone, CMC, crosslinked CMC and MC is considered critical to physical stability.

Surprisingly it was found that in case of the hydrophobic hydrolysis sensitive CETP inhibitor a converse effect could be observed. It was possible to stabilize both, the active pharmaceutical ingredient and the immediate release tablet by embedding the active in a hygroscopic polymeric matrix comprising of:

| Ingredient | Relative amount of tablet core [%] |
| --- | --- |
| CETP inhibitor thioester | >50% |
| Water insoluble, hygroscopic polymer | >40% |
| Water soluble, hygroscopic polymer | >4% |
| Other Excipients | <6% |

Furthermore, it was surprisingly found that increasing the amount of hydroscopic polymers from its usual range of 10 to 20% by weight to more than 30% by weight in the presence of hydrophobic compound did not lead to capping or cracking of the immediate-release tablet formulation as would have been expected. Therefore, the hydrophobic compound prevents the formation of cracks of the immediate release tablet when more than 30% by weight of the tablet consists of hygroscopic polymeric excipients.

In another embodiment, the present invention provides a composition comprising:
a) 48% to 55% by weight of CETP inhibitor thioester derivative; and
b) at least 30% of hygroscopic polymeric excipients by composition weight, preferably 44% to 50% by weight.

In another embodiment, the present invention provides a composition comprising:
a) 48% to 55% by weight of CETP inhibitor thioester derivative;
b) 40% to 45% by weight of water insoluble hygroscopic polymer; and
c) 4% to 5% by weight of water soluble hygroscopic polymer.

In certain embodiments of the present invention, at least two diluents with a bulk density lower than 800 g/L are microcrystalline cellulose and mannitol.

In certain embodiments of the present invention, at least two diluents with a bulk density lower than 800 g/L are microcrystalline cellulose and crospovidone micronized.

In certain embodiments of the present invention, microcrystalline cellulose and mannitol are present in a weight ratio of about 9:1 to 1:1.

In certain embodiments of the present invention, microcrystalline cellulose and micronized crospovidone are present in a weight ratio of about 5:1 to 5:3.

In another embodiment, the present invention provides a composition comprising:
48% to 55% by weight of a CETP inhibitor thiosester derivative; and
at least 30% by weight, preferably 44% to 50% by weight of hydroxypropylmethyl cellulose, croscarmellose sodium, microcrystalline cellulose and micronized crosslinked polyvinylpyrrolidone.

In another embodiment, the present invention provides a composition comprising:
a) 48% to 55% by weight of a CETP inhibitor thiosester derivative;
b) 4% to 8% by weight of croscarmellose sodium; and
c) 35% to 44% by weight of hydroxypropylmethyl cellulose, microcrystalline cellulose and crospovidone micronized.

In another embodiment, the present invention provides a composition comprising:
a) 48% to 55% by weight of a CETP inhibitor thiosester derivative;
b) less than 12% by weight of crospovidone micronized; and
c) 35% to 44% by weight of hydroxypropylmethyl cellulose, microcrystalline cellulose and croscarmellose sodium.

In another embodiment, the present invention provides a composition comprising:
a) a CETP inhibitor thiosester derivative, more particularly S-[2-([[1-(2-ethylbutyl)-cyclohexyl]-carbonyl]amino)phenyl]2-methylpropanethioate; and
b) croscarmellose sodium.

In another embodiment, the present invention provides a composition comprising:
a) a CETP inhibitor thiosester derivative, more particularly S-[2-([[1-(2-ethylbutyl)-cyclohexyl]-carbonyl]amino)phenyl]2-methylpropanethioate;
b) microcrystalline cellulose;
c) crospovidone micronized;
d) hydroxypropylmethyl cellulose; and
e) croscarmellose sodium.

In another embodiment, the present invention provides a composition comprising:
a) a CETP inhibitor thiosester derivative, more particularly S-[2-([[1-(2-ethylbutyl)-cyclohexyl]-carbonyl]amino)phenyl]2-methylpropanethioate;
b) mannitol;
c) crospovidone micronized;
d) hydroxypropylmethyl cellulose; and
e) croscarmellose sodium.

In another embodiment, the present invention provides a composition comprising:
a) a CETP inhibitor thiosester derivative, more particularly S-[2-([[1-(2-ethylbutyl)-cyclohexyl]-carbonyl]amino)phenyl]2-methylpropanethioate;
b) mannitol;
c) crospovidone micronized;
d) hydroxypropylmethyl cellulose;
e) croscarmellose sodium; and
f) micro crystalline cellulose.

In another embodiment the present invention provides a composition comprising:
a) 48% to 55% by weight of a CETP inhibitor thiosester derivative, more particularly S-[2-([[1-(2-ethylbutyl)-cyclohexyl]-carbonyl]amino)phenyl]2-ethylpropanethioate;

b) 24% to 26% by weight of microcrystalline cellulose;
c) 11% to 12% by weight of crospovidone micronized;
d) 4% to 5% by weight of hydroxypropylmethyl cellulose; and
e) 4% to 6% by weight of croscarmellose sodium.

In another embodiment the present invention provides a composition comprising:
a) 48% to 55% by weight of a CETP inhibitor thioester derivative, more particularly S-[2-([[1-(2-ethylbutyl)-cyclohexyl]-carbonyl]amino)phenyl]2-ethylpropanethioate;
b) 24% to 26% by weight of microcrystalline cellulose;
c) 11% to 12% by weight of crospovidone micronized;
d) 4% to 5% by weight of hydroxypropylmethyl cellulose;
e) 4% to 6% by weight of croscarmellose sodium;
f) 0 to 1% by weight of magnesium stearate;
g) 0 to 1% by weight of colloidal silicon dioxide; and
h) 0 to 1% by weight of sodium stearyl fumarate.

In another embodiment, the present invention provides a composition comprising:
a) 48% to 55% by weight of a CETP inhibitor thioester derivative, more particularly S-[2-([[1-(2-ethylbutyl)-cyclohexyl]-carbonyl]amino)phenyl]2-methylpropanethioate;
b) 10% to 14% by weight of mannitol;
c) 8% to 12% by weight of crospovidone micronized;
d) 2% to 6% by weight of hydroxypropylmethyl cellulose; and
e) 5% to 9% croscarmellose sodium.

In another embodiment, the present invention provides a composition comprising:
a) 48% to 55% by weight of a CETP inhibitor thioester derivative, more particularly S-[2-([[1-(2-ethylbutyl)-cyclohexyl]-carbonyl]amino)phenyl]2-methylpropanethioate;
b) 10% to 14% by weight of mannitol;
c) 8% to 12% by weight of crospovidone micronized;
d) 2% to 6% by weight of hydroxypropylmethyl cellulose;
e) 5% to 9% by weight of croscarmellose sodium; and
f) 11% to 15% by weight of microcrystalline cellulose.

In certain embodiments of the present invention, the composition is a pharmaceutical composition.

The pharmaceutical composition can be, for example, in the form of a pill, capsule or tablet, each containing a predetermined amount of CETP inhibitor thioester and in particular coated for ease of swallowing, in the form of a powder or granules. In particular, the pharmaceutical composition is in the form of a tablet comprising the CETP inhibitor thioesester derivative and the components of the tablet utilized and described therein. For oral administration, fine powders or granules may contain diluting, dispersing and/or surface active agents and may be present, for example, in capsules or sachets in the dry state, or in tablets wherein binders and lubricants may be included. Components such as sweeteners, flavoring agents, preservatives, suspending agents, thickening agents, and/or emulsifying agents also may be present in the pharmaceutical composition.

In a particular embodiment, the composition herein is film coated, with polyvinyl alcohol based coat (PVA-based coat), particularly with 20 mg or less PVA-based coat, more particularly with 15 mg PVA-based coat.

In certain embodiments of the present invention, the composition comprises 100 mg to 600 mg of S-[2-([[1-(2-ethylbutyl)-cyclohexyl]-carbonyl]amino)phenyl]2-methylpropanethioate. In particular, the composition comprises 150 mg to 450 mg of S-[2-([[1-(2-ethylbutyl)-cyclohexyl]-carbonyl]amino)phenyl]2-methylpropanethioate. More particularly, the composition comprises 250 mg to 350 mg of S-[2-([[1-(2-ethylbutyl)-cyclohexyl]-carbonyl]amino)phenyl]2-methylpropanethioate. Most particularly, the composition comprises 250 mg to 350 mg of S-[2-([[1-(2-ethylbutyl)-cyclohexyl]-carbonyl]amino)phenyl]2-methylpropanethioate.

In another embodiment of the present invention, the composition comprises for pediatric use 25 mg to 300 mg of S-[2-([[1-(2-ethylbutyl)-cyclohexyl]-carbonyl]amino)phenyl]2-methylpropanethioate. In particular the pediatric composition comprises 75 mg to 150 mg of S-[2-([[1-(2-ethylbutyl)-cyclohexyl]-carbonyl]amino)phenyl]2-methylpropanethioate.

The CETP inhibitor can be administered to the mammal at any suitable dosage (e.g., to achieve a therapeutically effective amount). For example, a suitable dose of a therapeutically effective amount of Compound I for administration to a patient will be between approximately 100 mg to about 1800 mg per day. A desirable dose is preferably about 300 mg to about 900 mg per day. A preferred dose is about 600 mg per day.

In another embodiment, the invention provides a kit comprising a pharmaceutical composition comprising a therapeutically effective amount of a CETP inhibitor thioester derivative and at least 30% by weight of hygroscopic polymeric excipients by composition weight, prescribing information also known as "leaflet", a blister package or bottle (HDPE or glass) and a container. The prescribing information preferably includes the advice to a patient regarding the administration of the CETP inhibitor thioester derivative (e.g. compound of formula (I')) with food, especially to improve the bioavailability of the CETP inhibitor thioester derivative.

In another embodiment the invention provides a kit comprising a composition as described therein, prescribing information also known as "leaflet", a blister package or bottle (HDPE or glass) and a container. The prescribing information preferably includes the advice to a patient regarding the administration of the CETP inhibitor thioester derivative (e.g. compound of formula (I')) with food, especially to improve the bioavailability of the CETP inhibitor thioester derivative.

In another embodiment, the invention provides a kit comprising a composition comprising a therapeutically effective amount of S-[2-([[1-(2-ethylbutyl)-cyclohexyl]-carbonyl]amino)phenyl]2-methylpropanethioate and at least 30% by weight of hygroscopic polymeric excipients by composition weight, prescribing information, a blister package or bottle and a container. In particular embodiments the invention provides the kit as described herein, wherein the prescribing information includes the advice to a patient regarding the administration of S-[2-([[1-(2-ethylbutyl)-cyclohexyl]-carbonyl]amino)phenyl]2-methylpropanethioate with food.

In another embodiment, the invention provides a tablet comprising the composition as herein described.

In another embodiment, the invention provides a composition as herein described for preparing a medicament for the treatment or prevention of cardiovascular disorder, in particular wherein the S-[2-([[1-(2-ethylbutyl)-cyclohexyl]-carbonyl]amino)phenyl]2-methylpropanethioate is administered at a daily dose of 100 mg to 1800 mg, particularly 300 mg to 900 mg, more particularly 600 mg, more particularly wherein S-[2-([[1-(2-ethylbutyl)-cyclohexyl]-carbonyl]amino)phenyl]2-methylpropanethioate is administered with food. In another embodiment the present invention provides a process for the preparation of the composition as described herein, which comprises the following steps:
a) Mixing and granulating, the water instable compound with a waxy consistency, crospovidone micronized, microcrystalline cellulose, croscarmellose sodium and optionally with hydroxypropylmethyl cellulose;

b) spraying up to 0.5% by weight of hydroxypropylmethyl cellulose in water or in 10%-30% ethanol by weight/70%-90% water by weight, more particularly in 20% ethanol by weight/80% water by weight onto the granulates obtained according to step a);
c) drying the granulates; and
d) blending microcrystalline cellulose, colloidal silicon dioxide and sodium stearylfumarate with the dry granulates obtained according to step c).

In another embodiment the present invention provides a process for the preparation of the composition as described herein, which comprises the following steps:
a) mixing and granulating, the water instable compound with a waxy consistency, crospovidone micronized, mannitol, croscarmellose sodium and hydroxypropylmethyl cellulose;
b) spraying up to 0.5% by weight of hydroxypropylmethyl cellulose in water or in 10%-30% ethanol by weight/70%-90% water by weight, more particularly in 20% ethanol by weight/80% water by weight onto the granulates obtained according to step a);
c) drying the granulates; and
d) blending microcrystalline cellulose, colloidal silicon dioxide and sodium stearylfumarate with the dry granulates obtained according to step c).

In another embodiment the present invention provides a process for the preparation of the composition as described herein, which comprises the following steps:
a) mixing and granulating, the water instable compound with a waxy consistency, crospovidone micronized, microcrystalline cellulose and croscarmellose sodium;
b) spraying the hydroxypropylmethyl cellulose in 10%-30% ethanol by weight/70%-90% water by weight, more particularly in 20% ethanol by weight/80% water by weight onto the granulates obtained according to step a);
c) drying the granulates; and
d) blending microcrystalline cellulose, colloidal silicon dioxide and sodium stearylfumarate with the dry granulates obtained according to step c).

In another embodiment the present invention provides a process for the preparation of the composition as described herein, which comprises the following steps:
a) mixing and granulating, the water instable compound with a waxy consistency, crospovidone micronized, microcrystalline cellulose, croscarmellose sodium and hydroxypropylmethyl cellulose;
b) spraying in the granulation fluid consisting of 10%-30% ethanol by weight/70%-90% water by weight, more particularly of 20% ethanol by weight/80% water by weight onto the granulates obtained according to step a);
c) drying the granulates;
d) blending microcrystalline cellulose, colloidal silicon dioxide and sodium stearylfumarate with the dry granulates obtained according to step c);
e) compressing the tablets;
f) preheating the tablets with inlet air ≤60° C. until a tablet temperature of around 43° C. is reached;
g) spraying the coating suspension Opadry® onto the tablets; and
h) drying the film-coated tablets under constant rotation in the perforated coating pan.

Manufacturing Process:

Herein, the API refers to the active substance which is hydrophobic, water instable compound with a waxy consistency, in particular to a CETP inhibitor thioester derivative, more particularly to a CETP inhibitor thioester derivative of formula (I) or (I'). In the examples 1 to 45, the API refers to thioisobutyric acid S-(2-{[1-(2-ethyl-butyl)-cyclohexanecarbonyl]-amino}-phenyl)ester of formula (I') in crystalline form.

The composition of the present invention may be prepared according to any known process which results in keeping the API substantially in crystalline form (the amount of the hydrophobic, API in amorphous does not exceed 10% by weight). Furthermore, the composition of the present invention may be prepared according to any known process which results in keeping the API substantially in crystalline form (the amount of the hydrophobic, water instable compound with a waxy consistency substantially in amorphous does not exceed 10% by weight).

The process for preparing a pharmaceutical composition according to the present invention may comprise the following steps:
1) dissolving hydroxypropylmethyl cellulose (0.5% by weight of total hydroxypropylmethyl cellulose) in 20% ethanol by weight and 80% water by weight under constant stirring;
2) loading granulator (high shear mixer: e.g. Diosna®) vertical granulator with bottom driven impeller, with a hydrophobic, water instable compound with a waxy consistency, crospovidone micronized, microcrystalline cellulose, croscarmellose sodium and remainder of hydroxypropylmethyl cellulose;
3) mixing the dry granulate components using impeller and chopper;
4) humidifying the granulate by spraying of the granulation fluid under constant mixing using impeller and chopper;
5) kneading the wetted granulate using impeller and chopper;
6) discharging the wet granulate, screening it over a conical mill [e.g. Frewitt® (screening mill with rotating impeller)); fitted with a 10 mm square screen and loading it into the fluid bed dryer
7) drying the granulate in the fluid bed dryer (e.g. Glatt®) with inlet air temperature ≤60° C. until the final LOD (loss on drying) of ≤3.5% by weight is reached;
8) discharging the dried granulate and milling it using an impact mill fitted with a 1.5 mm round perforation screen (e.g. Frewitt® (impact mill with rotating hammer);
9) adding the components of the external phase (e.g. microcrystalline cellulose, colloidal silicon dioxide and sodium stearylfumarate) over a sieve fitted with a 1 mm round perforation screen to the granulate
10) blending all the components in a bin blender (e.g. Tumblemix® (tumble blending in bin blender));
11) compressing the tablets on a rotary tablet press with low compression force (around 6 kN), (e.g. Korsch® (power assisted);
12) preparing the coating suspension by suspending Opadry® complete coating system in water under constant stirring;
13) loading the tablets into the perforated coating pan;
14) preheating the tablets with inlet air ≤60° C. until a tablet temperature of around 43° C. is reached under constant rotation of the perforated coating pan (e.g. Glatt® (perforated coating system));
15) spraying the coating suspension onto the tablets under constant rotation of the perforated coating pan;
16) drying the film-coated tablets under constant rotation in the perforated coating pan;
17) discharging the film-coated tablets.

Alternatively for example for the composition with hydroxypropylmethyl cellulose 6 cp, the process for preparing a pharmaceutical composition according to the present invention may comprise the following steps:

1) dissolving all hydroxypropylmethyl cellulose in 20% ethanol by weight and 80% water by weight under constant stirring;
2) loading granulator (high shear mixer: e.g. Diosna®) vertical granulator with bottom driven impeller, with a hydrophobic, water instable compound with a waxy consistency, crospovidone micronized, microcrystalline cellulose and croscarmellose sodium;
3) mixing the dry granulate components using impeller and chopper;
4) humidifying the granulate by spraying of the granulation fluid under constant mixing using impeller and chopper;
5) kneading the wetted granulate using impeller and chopper;
6) discharging the wet granulate, screening it over a conical mill (e.g. Frewitt® (screening mill with rotating impeller); fitted with a 10 mm square screen and loading it into the fluid bed dryer
7) drying the granulate in the fluid bed dryer (e.g. Glatt®) with inlet air temperature ≤60° C. until the final LOD (loss on drying) of ≤3.5% by weight is reached;
8) discharging the dried granulate and milling it using an impact mill fitted with a 1.5 mm round perforation screen (e.g. Frewitt® (impact mill with rotating hammer);
9) adding the components of the external phase (e.g. microcrystalline cellulose, colloidal silicon dioxide and sodium stearylfumarate) over a sieve fitted with a 1 mm round perforation screen to the granulate
10) blending all the components in a bin blender (e.g. Tumblemix® (tumble blending in bin blender));
11) compressing the tablets on a rotary tablet press with low compression force (around 6 kN), (e.g. Korsch® (power assisted);
12) preparing the coating suspension by suspending Opadry® complete coating system in water under constant stirring;
13) loading the tablets into the perforated coating pan;
14) preheating the tablets with inlet air ≤60° C. until a tablet temperature of around 43° C. is reached under constant rotation of the perforated coating pan (e.g. Glatt® (perforated coating system));
15) spraying the coating suspension onto the tablets under constant rotation of the perforated coating pan;
16) drying the film-coated tablets under constant rotation in the perforated coating pan; and
17) discharging the film-coated tablets.

Other features and embodiments of the invention will become apparent from the following examples which are given for illustration of the invention rather than for limiting its intended scope.

Examples 1 to 42 and placebo example A were prepared according to the above mentioned general processes, wherein the API for example A has been replaced with mannitol. Examples 1 to 42 were all film coated with 20 mg PVA-based coat (e.g. Opadry®).

Example No. 1

| Ingredient | Mass/Unit [mg] | Amount/Unit [%] | hygroscopic polymer Water insoluble | hygroscopic polymer Water soluble |
|---|---|---|---|---|
| API | 300.00 | 52.54 | N/A | N/A |
| Microcrystalline | 66 | 11.56 | + | |
| Cellulose (Type 101) | | | | |
| Crospovidone micronized | 66.00 | 11.56 | + | |
| HPMC (2910 3 cp) | 24.00 | 4.20 | | + |
| CMC Na | 34.00 | 5.95 | + | |
| Colloidal Silicon Dioxide | 3.00 | 0.53 | N/A | N/A |
| Sodium stearylfumarate | 3.00 | 0.53 | N/A | N/A |
| Microcrystalline Cellulose (Type 102) | 75.00 | 13.35 | + | |
| Total tablet | 571.00 | 100.00 | | |
| Amount hygroscopic polymers | | | 42.21% | 4.20% |
| Total amount hygroscopic polymers | | | 46.41% | |

Example No. 2

| Ingredient | Mass/Unit [mg] | Amount/Unit [%] | hygroscopic polymer Water insoluble | hygroscopic polymer Water soluble |
|---|---|---|---|---|
| API | 300.00 | 53.38 | N/A | N/A |
| Microcrystalline Cellulose (Type 101) | 66.00 | 11.74 | + | |
| Crospovidone micronized | 66.00 | 11.74 | + | |
| HPMC (2910 3 cp) | 24.00 | 4.27 | | + |
| CMC Na | 28.00 | 4.98 | + | |
| Sodium stearylfumarate | 3.00 | 0.53 | N/A | N/A |
| Microcrystalline Cellulose (Type 102) | 75.00 | 13.35 | + | |
| Total tablet | 562.00 | 100.00 | | |
| Amount hygroscopic polymers | | | 41.81% | 4.27% |
| Total amount hygroscopic polymers | | | 46.08% | |

Example No. 3

| Ingredient | Mass/Unit [mg] | Amount/Unit [%] | hygroscopic polymer Water insoluble | hygroscopic polymer Water soluble |
|---|---|---|---|---|
| API | 300.00 | 53.10 | N/A | N/A |
| Microcrystalline Cellulose (Type 101) | 66.00 | 11.68 | + | |
| Crospovidone micronized | 66.00 | 11.68 | + | |
| HPMC (2910 3 cp) | 24.00 | 4.25 | | + |
| CMC Na | 28.00 | 4.96 | + | |
| Sodium stearylfumarate | 3.00 | 0.53 | N/A | N/A |
| Magnesium Stearate | 3.00 | 0.53 | N/A | N/A |
| Microcrystalline Cellulose (Type 102) | 75.00 | 13.27 | + | |
| Total tablet | 565.00 | 100.00 | | |
| Amount hygroscopic polymers | | | 41.59% | 4.25% |
| Total amount hygroscopic polymers | | | 45.84% | |

Example No. 4

| Ingredient | Mass/Unit [mg] | Amount/Unit [%] | hygroscopic polymer Water insoluble | hygroscopic polymer Water soluble |
|---|---|---|---|---|
| API | 300.00 | 53.10 | N/A | N/A |
| Microcrystalline Cellulose (Type 101) | 66.00 | 11.68 | + | |
| Crospovidone micronized | 66.00 | 11.68 | + | |
| HPMC (2910 3 cp) | 24.00 | 4.25 | | + |
| CMC Na | 28.00 | 4.96 | + | |
| Sodium stearylfumarate | 3.00 | 0.53 | N/A | N/A |
| Colloidal Silicon Dioxide | 3.00 | 0.53 | N/A | N/A |
| Microcrystalline Cellulose (Type 102) | 75.00 | 13.27 | + | |
| Total tablet | 565.00 | 100.00 | | |
| Amount hygroscopic polymers | | | 41.59% | 4.25% |
| Total amount hygroscopic polymers | | | 45.84% | |

Example No. 5

| Ingredient | Mass/Unit [mg] | Amount/Unit [%] | hygroscopic polymer Water insoluble | hygroscopic polymer Water soluble |
|---|---|---|---|---|
| API | 300.00 | 52.82 | N/A | N/A |
| Microcrystalline Cellulose (Type 101) | 66.00 | 11.62 | + | |
| Crospovidone micronized | 66.00 | 11.62 | + | |
| HPMC (2910 3 cp) | 24.00 | 4.23 | | + |
| CMC Na | 34.00 | 5.99 | + | |
| Sodium stearylfumarate | 3.00 | 0.53 | N/A | N/A |
| Microcrystalline Cellulose (Type 102) | 75.00 | 13.20 | + | |
| Total tablet | 568.00 | 100.00 | | |
| Amount hygroscopic polymers | | | 42.43% | 4.23% |
| Total amount hygroscopic polymers | | | 46.65% | |

Example No. 6

| Ingredient | Mass/Unit [mg] | Amount/Unit [%] | hygroscopic polymer Water insoluble | hygroscopic polymer Water soluble |
|---|---|---|---|---|
| API | 300.00 | 52.54 | N/A | N/A |
| Microcrystalline Cellulose (Type 101) | 66.00 | 11.56 | + | |
| Crospovidone micronized | 66.00 | 11.56 | + | |
| HPMC (2910 3 cp) | 24.00 | 4.20 | | + |
| CMC Na | 34.00 | 5.95 | + | |
| Sodium stearylfumarate | 3.00 | 0.53 | N/A | N/A |
| Colloidal Silicon Dioxide | 3.00 | 0.53 | N/A | N/A |
| Microcrystalline Cellulose (Type 102) | 75.00 | 13.13 | + | |
| Total tablet | 571.00 | 100.00 | | |
| Amount hygroscopic polymers | | | 42.21% | 4.20% |
| Total amount hygroscopic polymers | | | 46.41% | |

Example No. 7

| Ingredient | Mass/Unit [mg] | Amount/Unit [%] | hygroscopic polymer Water insoluble | hygroscopic polymer Water soluble |
|---|---|---|---|---|
| API | 300.00 | 52.34 | N/A | N/A |
| Microcrystalline Cellulose (Type 101) | 66.00 | 11.51 | + | |
| Crospovidone micronized | 66.00 | 11.51 | + | |
| HPMC (2910 3 cp) | 24.00 | 4.19 | | + |
| CMC Na | 36.20 | 6.32 | + | |
| Sodium stearylfumarate | 3.00 | 0.52 | N/A | N/A |
| Colloidal Silicon Dioxide | 3.00 | 0.52 | N/A | N/A |
| Microcrystalline Cellulose (Type 102) | 75.00 | 13.08 | + | |
| Total tablet | 573.20 | 100.00 | | |
| Amount hygroscopic polymers | | | 42.43% | 4.19% |
| Total amount hygroscopic polymers | | | 46.62% | |

Example No. 8

| Ingredient | Mass/Unit [mg] | Amount/Unit [%] | hygroscopic polymer Water insoluble | hygroscopic polymer Water soluble |
|---|---|---|---|---|
| API | 300.00 | 51.99 | N/A | N/A |
| Microcrystalline Cellulose (Type 102) | 75.00 | 13.00 | + | |
| Crospovidone micronized | 60.00 | 10.40 | + | |
| HPMC (2910 3 cp) | 24.00 | 4.16 | | + |
| Mannitol | 72.00 | 12.48 | N/A | N/A |
| CMC Na | 40.00 | 6.93 | + | |
| Colloidal Silicon Dioxide | 3.00 | 0.52 | N/A | N/A |
| Sodium stearylfumarate | 3.00 | 0.52 | N/A | N/A |
| Total tablet | 577.00 | 100.00 | | |
| Amount hygroscopic polymers | | | 30.33% | 4.16% |
| Total amount hygroscopic polymers | | | 34.49% | |

Example No. 9

| Ingredient | Mass/Unit [mg] | Amount/Unit [%] | hygroscopic polymer Water insoluble | hygroscopic polymer Water soluble |
|---|---|---|---|---|
| API | 300.00 | 55.58 | N/A | N/A |
| Microcrystalline Cellulose (Type 101) | 67.00 | 12.41 | + | |
| Crospovidone micronized | 67.00 | 12.41 | + | |
| HPMC (2910 3 cp) | 18.00 | 3.33 | | + |
| Microcrystalline Cellulose (Type 102) | 50.00 | 9.26 | + | |
| CMC Na | 27.00 | 5.00 | + | |
| Glycerylbehenate | 10.80 | 2.00 | N/A | N/A |
| Total tablet | 539.80 | 100.00 | | |
| Amount hygroscopic polymers | | | 39.09% | 3.33% |
| Total amount hygroscopic polymers | | | 42.42% | |

Example No. 10

| Ingredient | Mass/Unit [mg] | Amount/Unit [%] | hygroscopic polymer Water insoluble | hygroscopic polymer Water soluble |
|---|---|---|---|---|
| API | 300.00 | 50.77 | N/A | N/A |
| Microcrystalline Cellulose (Type 101) | 67.00 | 11.34 | + | |
| Crospovidone micronized | 67.00 | 11.34 | + | |
| HPMC (2910 3 cp) | 18.00 | 3.05 | | + |
| Microcrystalline Cellulose (Type 102) | 100.00 | 16.92 | + | |
| CMC Na | 27.00 | 4.57 | + | |
| Glycerylbehenate | 11.85 | 2.01 | N/A | N/A |
| Total tablet | 590.85 | 100.00 | | |
| Amount hygroscopic polymers [%] | | | 44.17% | 3.05% |
| Total amount hygroscopic polymers [%] | | | 47.22% | |

Example No. 11

| Ingredient | Mass/Unit [mg] | Amount/Unit [%] | hygroscopic polymer Water insoluble | hygroscopic polymer Water soluble |
|---|---|---|---|---|
| API | 300.00 | 53.10 | N/A | N/A |
| Microcrystalline Cellulose (Type 101) | 69.00 | 12.21 | + | |
| Crospovidone micronized | 69.00 | 12.21 | + | |
| HPMC (2910 3 cp) | 21.00 | 3.72 | | + |
| Microcrystalline Cellulose (Type 102) | 75.00 | 13.27 | + | |
| CMC Na | 28.00 | 4.95 | + | |
| Sodium Stearylfumarate | 3.00 | 0.53 | N/A | N/A |
| Total tablet | 565.00 | 100.00 | | |
| Amount hygroscopic polymers [%] | | | 42.64% | 3.72% |
| Total amount hygroscopic polymers [%] | | | 46.36% | |

Example No. 12

| Ingredient | Mass/Unit [mg] | Amount/Unit [%] | hygroscopic polymer Water insoluble | hygroscopic polymer Water soluble |
|---|---|---|---|---|
| API | 300.00 | 53.67 | N/A | N/A |
| Microcrystalline Cellulose (Type 101) | 69.00 | 12.34 | + | |
| Crospovidone micronized | 69.00 | 12.34 | + | |
| HPMC (2910 3 cp) | 21.00 | 3.76 | | + |
| Microcrystalline Cellulose (Type 102) | 75.00 | 13.42 | + | |
| CMC Na | 22.00 | 3.94 | + | |
| Sodium Stearylfumarate | 3.00 | 0.54 | N/A | N/A |
| Total tablet | 559.00 | 100.00 | | |
| Amount hygroscopic polymers | | | 42.04% | 3.76% |
| Total amount hygroscopic polymers | | | 45.80% | |

Example No. 13

| Ingredient | Mass/Unit [mg] | Amount/Unit [%] | hygroscopic polymer Water insoluble | hygroscopic polymer Water soluble |
|---|---|---|---|---|
| API | 300.00 | 52.91 | N/A | N/A |
| Microcrystalline Cellulose (Type 101) | 69.00 | 12.17 | + | |
| Crospovidone micronized | 69.00 | 12.17 | + | |
| HPMC (2910 3 cp) | 21.00 | 3.70 | | + |
| Microcrystalline Cellulose (Type 102) | 75.00 | 13.23 | + | |
| CMC Na | 22.00 | 3.88 | + | |
| Sodium Stearylfumarate | 3.00 | 0.53 | N/A | N/A |
| Talc | 8.00 | 1.41 | N/A | N/A |
| Total tablet | 567.00 | 100.00 | | |
| Amount hygroscopic polymers | | | 41.45% | 3.70% |
| Total amount hygroscopic polymers | | | 45.15% | |

Example No. 14

| Ingredient | Mass/Unit [mg] | Amount/Unit [%] | hygroscopic polymer Water insoluble | hygroscopic polymer Water soluble |
|---|---|---|---|---|
| API | 300.00 | 53.38 | N/A | N/A |
| Microcrystalline Cellulose (Type 101) | 66.00 | 11.74 | + | |
| Crospovidone micronized | 66.00 | 11.74 | + | |
| HPMC (2910 3 cp) | 24.00 | 4.27 | | + |
| CMC Na | 28.00 | 4.98 | + | |
| Microcrystalline Cellulose (Type 200) | 75.00 | 13.35 | + | |
| Sodium Stearylfumarate | 3.00 | 0.53 | N/A | N/A |
| Total tablet | 562.00 | 100.00 | | |
| Amount hygroscopic polymers | | | 41.81% | 4.27% |
| Total amount hygroscopic polymers | | | 46.09% | |

Example No. 15

| Ingredient | Mass/Unit [mg] | Amount/Unit [%] | hygroscopic polymer Water insoluble | hygroscopic polymer Water soluble |
|---|---|---|---|---|
| API | 300.00 | 53.38 | N/A | N/A |
| Microcrystalline Cellulose (Type 101) | 66.00 | 11.74 | + | |
| Crospovidone micronized | 66.00 | 11.74 | + | |
| HPMC (2910 3 cp) | 24.00 | 4.27 | | + |
| CMC Na | 28.00 | 4.98 | + | |
| Silicified Microcrystalline Cellulose (Type Prosolv SMCC 90) | 75.00 | 13.35 | + | |
| Sodium Stearylfumarate | 3.00 | 0.53 | N/A | N/A |
| Total tablet | 562.00 | 100.00 | | |
| Amount hygroscopic polymers | | | 41.81% | 4.27% |
| Total amount hygroscopic polymers | | | 46.09% | |

Example No. 16

| Ingredient | Mass/Unit [mg] | Amount/Unit [%] | hygroscopic polymer Water insoluble | hygroscopic polymer Water soluble |
|---|---|---|---|---|
| API | 300.00 | 54.84 | N/A | N/A |
| Microcrystalline Cellulose (Type 101) | 90.00 | 16.45 | + | |
| Crospovidone micronized | 119.80 | 21.90 | + | |
| HPMC (2910 6 cp) | 18.00 | 3.29 | | + |
| Talc | 18.00 | 3.29 | N/A | N/A |
| Magnesium Stearate | 1.20 | 0.22 | N/A | N/A |
| Total tablet | 547.00 | 100.00 | | |
| Amount hygroscopic polymers | | | 38.35% | 3.29% |
| Total amount hygroscopic polymers | | | 41.65% | |

Example No. 17

| Ingredient | Mass/Unit [mg] | Amount/Unit [%] | hygroscopic polymer Water insoluble | hygroscopic polymer Water soluble |
|---|---|---|---|---|
| API | 300.00 | 55.66 | N/A | N/A |
| Microcrystalline Cellulose (Type 101) | 90.00 | 16.70 | + | |
| Crospovidone micronized | 119.80 | 22.23 | + | |
| HPMC (2910 6 cp) | 18.00 | 3.34 | | + |
| Glycerylbehenate | 11.20 | 2.08 | N/A | N/A |
| Total tablet | 539.0 | 100.00 | | |
| Amount hygroscopic polymers | | | 38.92% | 3.34% |
| Total amount hygroscopic polymers | | | 42.26% | |

Example No. 18

| Ingredient | Mass/Unit [mg] | Amount/Unit [%] | hygroscopic polymer Water insoluble | hygroscopic polymer Water soluble |
|---|---|---|---|---|
| API | 300.00 | 55.72 | N/A | N/A |
| Microcrystalline Cellulose (Type 101) | 100.00 | 18.57 | + | |
| Crospovidone micronized | 59.20 | 11.00 | + | |
| HPMC (2910 6 cp) | 18.00 | 3.34 | | + |
| low substituted HPC | 50.00 | 9.29 | + | |
| Glycerylbehenate | 11.20 | 2.08 | N/A | N/A |
| Total tablet | 538.40 | 100.00 | | |
| Amount hygroscopic polymers | | | 38.86% | 3.34% |
| Total amount hygroscopic polymers | | | 42.20% | |

Example No. 19

| Ingredient | Mass/Unit [mg] | Amount/Unit [%] | hygroscopic polymer Water insoluble | hygroscopic polymer Water soluble |
|---|---|---|---|---|
| API | 300.00 | 55.66 | N/A | N/A |
| Mannitol | 100.00 | 18.55 | N/A | N/A |
| Crospovidone micronized | 59.80 | 11.09 | + | |
| HPMC (2910 3 cp) | 18.00 | 3.34 | | + |

-continued

| Ingredient | Mass/Unit [mg] | Amount/Unit [%] | hygroscopic polymer Water insoluble | hygroscopic polymer Water soluble |
|---|---|---|---|---|
| Microcrystalline Cellulose (Type 200) | 50.00 | 9.28 | + | |
| Glycerylbehenate | 11.20 | 2.08 | N/A | N/A |
| Total tablet | 539.00 | 100.00 | | |
| Amount hygroscopic polymers | | | 31.73% | 12.62% |
| Total amount hygroscopic polymers | | | 44.34% | |

Example No. 20

| Ingredient | Mass/Unit [mg] | Amount/Unit [%] | hygroscopic polymer Water insoluble | hygroscopic polymer Water soluble |
|---|---|---|---|---|
| API | 300.00 | 55.66 | N/A | N/A |
| Mannitol | 100.00 | 18.55 | N/A | N/A |
| Crospovidone micronized | 59.80 | 11.09 | + | |
| HPMC (2910 3 cp) | 18.00 | 3.34 | | + |
| Microcrystalline Cellulose (Type 200) | 50.00 | 9.28 | + | |
| Sodium Stearylfumarate | 11.20 | 2.08 | N/A | N/A |
| Total tablet | 539.00 | 100.00 | | |
| Amount hygroscopic polymers | | | 31.73% | 12.62% |
| Total amount hygroscopic polymers | | | 44.34% | |

Example No. 21

| Ingredient | Mass/Unit [mg] | Amount/Unit [%] | hygroscopic polymer Water insoluble | hygroscopic polymer Water soluble |
|---|---|---|---|---|
| API | 300.00 | 56.56 | N/A | N/A |
| Mannitol | 100.00 | 18.85 | N/A | N/A |
| Crospovidone micronized | 59.80 | 11.27 | + | |
| HPMC (2910 3 cp) | 18.00 | 3.39 | | + |
| Microcrystalline Cellulose (Type 200) | 50.00 | 9.43 | + | |
| Sodium Stearylfumarate | 2.65 | 0.50 | N/A | N/A |
| Total tablet | 530.45 | 100.00 | | |
| Amount hygroscopic polymers | | | 30.62% | 12.82% |
| Total amount hygroscopic polymers | | | 43.44% | |

Example No. 22

| Ingredient | Mass/Unit [mg] | Amount/Unit [%] | hygroscopic polymer Water insoluble | hygroscopic polymer Water soluble |
|---|---|---|---|---|
| API | 300.00 | 56.60 | N/A | N/A |
| Mannitol | 100.00 | 18.87 | N/A | N/A |
| Crospovidone micronized | 59.80 | 11.28 | + | |
| HPMC (2910 3 cp) | 18.00 | 3.40 | | + |
| Microcrystalline Cellulose (Type 200) | 50.00 | 9.43 | + | |
| Sodium Stearylfumarate | 2.24 | 0.42 | N/A | N/A |
| Total tablet | 530.04 | 100.00 | | |
| Amount hygroscopic polymers | | | 30.57% | 12.83% |
| Total amount hygroscopic polymers | | | 43.40% | |

Example No. 23

| Ingredient | Mass/Unit [mg] | Amount/Unit [%] | hygroscopic polymer Water insoluble | hygroscopic polymer Water soluble |
|---|---|---|---|---|
| API | 300.00 | 56.56 | N/A | N/A |
| Mannitol | 100.00 | 18.85 | N/A | N/A |
| Crospovidone micronized | 59.80 | 11.27 | + | |
| HPMC (2910 3 cp) | 18.00 | 3.39 | | + |
| Microcrystalline Cellulose (Type 200) | 25.00 | 4.71 | + | |
| low substituted HPC | 25.00 | 4.71 | + | |
| Sodium Stearylfumarate | 2.65 | 0.50 | N/A | N/A |
| Total tablet | 530.45 | 100.00 | | |
| Amount hygroscopic polymers | | | 20.70% | 3.39% |
| Total amount hygroscopic polymers | | | 24.09% | |

Example No. 24

| Ingredient | Mass/Unit [mg] | Amount/Unit [%] | hygroscopic polymer Water insoluble | hygroscopic polymer Water soluble |
|---|---|---|---|---|
| API | 300.00 | 55.17 | N/A | N/A |
| Mannitol | 100.00 | 18.39 | N/A | N/A |
| Crospovidone micronized | 59.80 | 11.00 | + | |
| HPMC (2910 6 cp) | 18.00 | 3.31 | | + |
| Microcrystalline Cellulose (Type 200) | 50.222 | 9.223 | + | |
| Talc | 4.78 | 0.88 | N/A | N/A |
| Glycerylbehenate | 11.20 | 2.06 | N/A | N/A |
| Total tablet | 544.00 | 100.04 | | |
| Amount hygroscopic polymers | | | 20.19% | 3.31% |
| Total amount hygroscopic polymers | | | 23.50% | |

Example No. 25

| Ingredient | Mass/Unit [mg] | Amount/Unit [%] | hygroscopic polymer Water insoluble | hygroscopic polymer Water soluble |
|---|---|---|---|---|
| API | 300.00 | 55.66 | N/A | N/A |
| Mannitol | 100.00 | 18.55 | N/A | N/A |
| Crospovidone micronized | 59.80 | 11.09 | + | |
| HPMC (2910 6 cp) | 18.00 | 3.34 | | + |
| Microcrystalline Cellulose (Type 200) | 50.00 | 9.28 | + | |
| Glycerylbehenate | 11.20 | 2.08 | N/A | N/A |
| Total tablet | 539.00 | 100.00 | | |
| Amount hygroscopic polymers | | | 20.37% | 3.34% |
| Total amount hygroscopic polymers | | | 23.71% | |

Example No. 26

| Ingredient | Mass/Unit [mg] | Amount/Unit [%] | hygroscopic polymer Water insoluble | hygroscopic polymer Water soluble |
|---|---|---|---|---|
| API | 300.00 | 55.66 | N/A | N/A |
| Mannitol | 100.00 | 18.55 | N/A | N/A |
| Crospovidone micronized | 59.80 | 11.09 | + | |
| HPMC (2910 6 cp) | 18.00 | 3.34 | | + |
| Microcrystalline Cellulose (Type 200) | 50.00 | 9.28 | + | |
| Sodium Stearylfumarate | 11.20 | 2.08 | N/A | N/A |
| Total tablet | 539.00 | 100.00 | | |
| Amount hygroscopic polymers | | | 20.37% | 3.34% |
| Total amount hygroscopic polymers | | | 23.71% | |

Example No. 27

| Ingredient | Mass/Unit [mg] | Amount/Unit [%] | hygroscopic polymer Water insoluble | hygroscopic polymer Water soluble |
|---|---|---|---|---|
| API | 300.00 | 55.70 | N/A | N/A |
| Mannitol | 73.00 | 13.55 | N/A | N/A |
| Crospovidone micronized | 59.80 | 11.10 | + | |
| HPMC (2910 3 cp) | 18.00 | 3.34 | | + |
| CMC Na | 27.00 | 5.01 | + | |
| Microcrystalline Cellulose (Type 102) | 50.00 | 9.28 | + | |
| Glycerylbehenate | 10.80 | 2.01 | N/A | N/A |
| Total tablet | 538.60 | 100.00 | | |
| Amount hygroscopic polymers | | | 25.40% | 3.34% |
| Total amount hygroscopic polymers | | | 28.74% | |

Example No. 28

| Ingredient | Mass/Unit [mg] | Amount/Unit [%] | hygroscopic polymer Water insoluble | hygroscopic polymer Water soluble |
|---|---|---|---|---|
| API | 300.00 | 50.88 | N/A | N/A |
| Mannitol | 73.00 | 12.38 | N/A | N/A |
| Crospovidone micronized | 59.80 | 10.14 | + | |
| HPMC (2910 3 cp) | 18.00 | 3.05 | | + |
| CMC Na | 27.00 | 4.58 | + | |
| Microcrystalline Cellulose (Type 102) | 100.00 | 16.96 | + | |
| Glycerylbehenate | 11.80 | 2.00 | N/A | N/A |
| Total tablet | 589.60 | 100.00 | | |
| Amount hygroscopic polymers | | | 31.68% | 3.05% |
| Total amount hygroscopic polymers | | | 34.74% | |

Example No. 29

| Ingredient | Mass/Unit [mg] | Amount/Unit [%] | hygroscopic polymer Water insoluble | hygroscopic polymer Water soluble |
|---|---|---|---|---|
| API | 300.00 | 52.63 | N/A | N/A |
| Mannitol | 73.00 | 12.81 | N/A | N/A |
| Crospovidone micronized | 60.00 | 10.53 | + | |
| HPMC (2910 3 cp) | 18.00 | 3.16 | | + |
| CMC Na | 27.00 | 4.74 | + | |
| Microcrystalline Cellulose (Type 102) | 75.00 | 13.16 | + | |
| Glycerylbehenate | 17.00 | 2.98 | N/A | N/A |
| Total tablet | 570.00 | 100.00 | | |
| Amount hygroscopic polymers | | | 28.42% | 3.16% |
| Total amount hygroscopic polymers | | | 31.58% | |

Example No. 30

| Ingredient | Mass/Unit [mg] | Amount/Unit [%] | hygroscopic polymer Water insoluble | hygroscopic polymer Water soluble |
|---|---|---|---|---|
| API | 300.00 | 50.34 | N/A | N/A |
| Mannitol | 73.00 | 12.25 | N/A | N/A |
| Crospovidone micronized | 60.00 | 10.07 | + | |
| HPMC (2910 3 cp) | 18.00 | 3.02 | | + |
| CMC Na | 27.00 | 4.53 | + | |
| Microcrystalline Cellulose (Type 102) | 100.00 | 16.78 | + | |
| Glycerylbehenate | 18.00 | 3.02 | N/A | N/A |
| Total tablet | 596.00 | 100.00 | | |
| Amount hygroscopic polymers | | | 31.38% | 3.02% |
| Total amount hygroscopic polymers | | | 34.40% | |

Example No. 31

| Ingredient | Mass/Unit [mg] | Amount/Unit [%] | hygroscopic polymer Water insoluble | hygroscopic polymer Water soluble |
|---|---|---|---|---|
| API | 300.00 | 55.66 | N/A | N/A |
| Mannitol | 94.60 | 17.55 | N/A | N/A |
| Crospovidone micronized | 60.00 | 11.13 | + | |
| HPMC (2910 3 cp) | 18.00 | 3.34 | | + |
| CMC Na | 5.40 | 1.00 | + | |
| Microcrystalline Cellulose (Type 102) | 50.00 | 9.28 | + | |
| Glycerylbehenate | 11.00 | 2.04 | N/A | N/A |
| Total tablet | 539.00 | 100.00 | | |
| Amount hygroscopic polymers | | | 21.41% | 3.34% |
| Total amount hygroscopic polymers | | | 24.75% | |

Example No. 32

| Ingredient | Mass/Unit [mg] | Amount/Unit [%] | hygroscopic polymer Water insoluble | hygroscopic polymer Water soluble |
|---|---|---|---|---|
| API | 300.00 | 55.66 | N/A | N/A |
| Mannitol | 83.80 | 15.55 | N/A | N/A |
| Crospovidone micronized | 60.00 | 11.13 | + | |
| HPMC (2910 3 cp) | 18.00 | 3.34 | | + |
| CMC Na | 16.20 | 3.01 | + | |
| Microcrystalline Cellulose (Type 102) | 50.00 | 9.28 | + | |
| Glycerylbehenate | 11.00 | 2.04 | N/A | N/A |
| Total tablet | 539.00 | 100.00 | | |
| Amount hygroscopic polymers | | | 23.42% | 3.34% |
| Total amount hygroscopic polymers | | | 26.76% | |

Example No. 33

| Ingredient | Mass/Unit [mg] | Amount/Unit [%] | hygroscopic polymer Water insoluble | hygroscopic polymer Water soluble |
|---|---|---|---|---|
| API | 300.00 | 55.66 | N/A | N/A |
| Mannitol | 100.00 | 18.55 | N/A | N/A |
| Crospovidone micronized | 59.20 | 10.98 | + | |
| HPMC (2910 6 cp) | 18.00 | 3.34 | | + |
| low substituted HPC | 50.00 | 9.28 | + | |
| Glycerylbehenate | 11.20 | 2.08 | N/A | N/A |
| Total tablet | 539.00 | 100.00 | | |
| Amount hygroscopic polymers | | | 20.26 | 3.34 |
| Total amount hygroscopic polymers | | | 23.60 | |

Example No. 34

| Ingredient | Mass/Unit [mg] | Amount/Unit [%] | hygroscopic polymer Water insoluble | hygroscopic polymer Water soluble |
|---|---|---|---|---|
| API | 300.00 | 54.84 | N/A | N/A |
| Mannitol | 100.00 | 18.28 | N/A | N/A |
| Crospovidone micronized | 59.80 | 10.93 | + | |
| HPMC (2910 6 cp) | 18.00 | 3.29 | | + |
| low substituted HPC | 50.00 | 9.14 | + | |
| Talc | 18.00 | 3.29 | N/A | N/A |
| Magnesium Stearate | 1.20 | 0.22 | N/A | N/A |
| Total tablet | 547.00 | 100.00 | | |
| Amount hygroscopic polymers | | | 20.07% | 3.29% |
| Total amount hygroscopic polymers | | | 23.36% | |

Example No. 35

| Ingredient | Mass/Unit [mg] | Amount/Unit [%] | hygroscopic polymer Water insoluble | hygroscopic polymer Water soluble |
|---|---|---|---|---|
| API | 300.00 | 53.38 | N/A | N/A |
| Mannitol | 72.00 | 12.81 | N/A | N/A |
| Crospovidone micronized | 60.00 | 10.68 | + | |
| HPMC (2910 3 cp) | 24.00 | 4.27 | | + |
| CMC Na | 28.00 | 4.98 | + | |
| Microcrystalline Cellulose (Type 102) | 75.00 | 13.35 | + | |
| Sodium Stearylfumarate | 3.00 | 0.53 | N/A | N/A |
| Total tablet | 562.00 | 100.00 | | |
| Amount hygroscopic polymers | | | 29.01% | 4.27% |
| Total amount hygroscopic polymers | | | 33.28% | |

Example No. 36

| Ingredient | Mass/Unit [mg] | Amount/Unit [%] | hygroscopic polymer Water insoluble | hygroscopic polymer Water soluble |
|---|---|---|---|---|
| API | 300.00 | 51.99 | N/A | N/A |
| Mannitol | 72.00 | 12.48 | N/A | N/A |
| Crospovidone micronized | 60.00 | 10.40 | + | |
| HPMC (2910 3 cp) | 24.00 | 4.16 | | + |
| CMC Na | 40.00 | 6.93 | + | |
| Microcrystalline Cellulose (Type 102) | 75.00 | 13.00 | + | |
| Sodium Stearylfumarate | 3.00 | 0.52 | N/A | N/A |
| Colloidal Silicon Dioxide | 3.00 | 0.52 | N/A | N/A |
| Total tablet | 577.00 | 100.00 | | |
| Amount hygroscopic polymers | | | 30.33% | 4.16% |
| Total amount hygroscopic polymers | | | 34.49% | |

Example No. 37

| Ingredient | Mass/Unit [mg] | Amount/Unit [%] | hygroscopic polymer Water insoluble | hygroscopic polymer Water soluble |
|---|---|---|---|---|
| API | 300.00 | 52.82 | N/A | N/A |
| Mannitol | 72.00 | 12.68 | N/A | N/A |
| Crospovidone micronized | 60.00 | 10.56 | + | |
| HPMC (2910 3 cp) | 24.00 | 4.23 | | + |
| CMC Na | 28.00 | 4.93 | + | |
| Microcrystalline Cellulose (Type 102) | 75.00 | 13.20 | + | |
| Sodium Stearylfumarate | 3.00 | 0.53 | N/A | N/A |
| CMC Na | 6.00 | 1.06 | + | |
| Total tablet | 568.00 | 100.00 | | |
| Amount hygroscopic polymers | | | 29.75% | 4.23% |
| Total amount hygroscopic polymers | | | 33.98% | |

Example No. 38

| Ingredient | Mass/Unit [mg] | Amount/Unit [%] | hygroscopic polymer Water insoluble | hygroscopic polymer Water soluble |
|---|---|---|---|---|
| API | 300.00 | 53.38 | N/A | N/A |
| Mannitol | 72.00 | 12.81 | N/A | N/A |
| Crospovidone micronized | 60.00 | 10.68 | + | |
| HPMC (2910 3 cp) | 24.00 | 4.27 | | + |
| CMC Na | 28.00 | 4.98 | + | |
| Microcrystalline Cellulose (Type 102) | 75.00 | 13.35 | + | |
| Sodium Stearylfumarate | 3.00 | 0.53 | N/A | N/A |
| Total tablet | 562.00 | 100.00 | | |
| Amount hygroscopic polymers | | | 29.00% | 4.27% |
| Total amount hygroscopic polymers | | | 33.27% | |

Example No. 39

| Ingredient | Mass/Unit [mg] | Amount/Unit [%] | hygroscopic polymer Water insoluble | hygroscopic polymer Water soluble |
|---|---|---|---|---|
| API | 300.00 | 53.10 | N/A | N/A |
| Mannitol | 78.00 | 13.81 | N/A | N/A |
| Crospovidone micronized | 60.00 | 10.62 | + | |
| HPMC (2910 3 cp) | 21.00 | 3.72 | | + |
| CMC Na | 22.00 | 3.89 | + | |
| Microcrystalline Cellulose (Type 102) | 75.00 | 13.27 | + | |
| Sodium Stearylfumarate | 3.00 | 0.53 | N/A | N/A |
| CMC Na | 6.00 | 1.06 | + | |
| Total tablet | 565.00 | 100.00 | | |
| Amount hygroscopic polymers | | | 28.85% | 3.72% |
| Total amount hygroscopic polymers | | | 32.57% | |

Example No. 40

| Ingredient | Mass/Unit [mg] | Amount/Unit [%] | hygroscopic polymer Water insoluble | hygroscopic polymer Water soluble |
|---|---|---|---|---|
| API | 300.00 | 53.16 | N/A | N/A |
| Mannitol | 83.80 | 14.85 | N/A | N/A |
| Crospovidone micronized | 60.00 | 10.63 | + | |
| HPMC (2910 3 cp) | 18.00 | 3.19 | | + |
| CMC Na | 16.20 | 2.87 | + | |
| Microcrystalline Cellulose (Type 102) | 75.00 | 13.29 | + | |
| Sodium Stearylfumarate | 11.30 | 2.00 | N/A | N/A |
| Total tablet | 564.30 | 100.00 | | |
| Amount hygroscopic polymers | | | 26.79% | 3.19% |
| Total amount hygroscopic polymers | | | 29.98% | |

Example No. 41

| Ingredient | Mass/Unit [mg] | Amount/Unit [%] | hygroscopic polymer Water insoluble | hygroscopic polymer Water soluble |
|---|---|---|---|---|
| API | 300.00 | 53.98 | N/A | N/A |
| Mannitol | 83.80 | 15.08 | N/A | N/A |
| Crospovidone micronized | 60.00 | 10.80 | + | |
| HPMC (2910 3 cp) | 18.00 | 3.24 | | + |
| CMC Na | 16.20 | 2.91 | + | |
| Microcrystalline Cellulose (Type 102) | 75.00 | 13.49 | + | |
| Sodium Stearylfumarate | 2.80 | 0.50 | N/A | N/A |
| Total tablet | 555.80 | 100.00 | | |
| Amount hygroscopic polymers | | | 27.20% | 3.24% |
| Total amount hygroscopic polymers | | | 30.44% | |

Example No. 42

| Ingredient | Mass/Unit [mg] | Amount/Unit [%] | hygroscopic polymer Water insoluble | hygroscopic polymer Water soluble |
|---|---|---|---|---|
| API | 300.00 | 60.12 | N/A | N/A |
| Crospovidone micronized | 119.80 | 24.01 | + | |

-continued

| Ingredient | Mass/ Unit [mg] | Amount/ Unit [%] | hygroscopic polymer Water insoluble | hygroscopic polymer Water soluble |
|---|---|---|---|---|
| HPMC (2910 3 cp) | 18.00 | 3.61 | | + |
| Microcrystalline Cellulose (Type 200) | 50.00 | 10.02 | + | |
| Sodium Stearylfumarate | 11.20 | 2.24 | N/A | N/A |
| Total tablet | 499.00 | 100.00 | | |
| Amount hygroscopic polymers | | | 34.03% | 3.61% |
| Total amount hygroscopic polymers | | | 37.64% | |

Example A

| Ingredient | Mass/ Unit [mg] | Amount/ Unit [%] | hygroscopic polymer Water insoluble | hygroscopic polymer Water soluble |
|---|---|---|---|---|
| Mannitol | 300.00 | 52.54 | N/A | N/A |
| Microcrystalline Cellulose | 141.00 | 24.69 | + | |
| Crospovidone micronized | 66.00 | 11.56 | + | |
| HPMC | 24.00 | 4.20 | | + |
| CMC Na | 34.00 | 5.95 | | + |
| Colloidal Silicon Dioxide | 3.00 | 0.53 | N/A | N/A |
| Sodium stearylfumarate | 3.00 | 0.53 | N/A | N/A |
| Total tablet | 571.00 | 100.00 | | |
| Amount hygroscopic polymers | | | 42.21% | 4.20% |
| Total amount hygroscopic polymers | | | 46.41% | |

Example B

Figure 2:
FIG. 2 is a 3D reconstruction of all X-ray slices of a tablet according to placebo example A.
Figure 3:
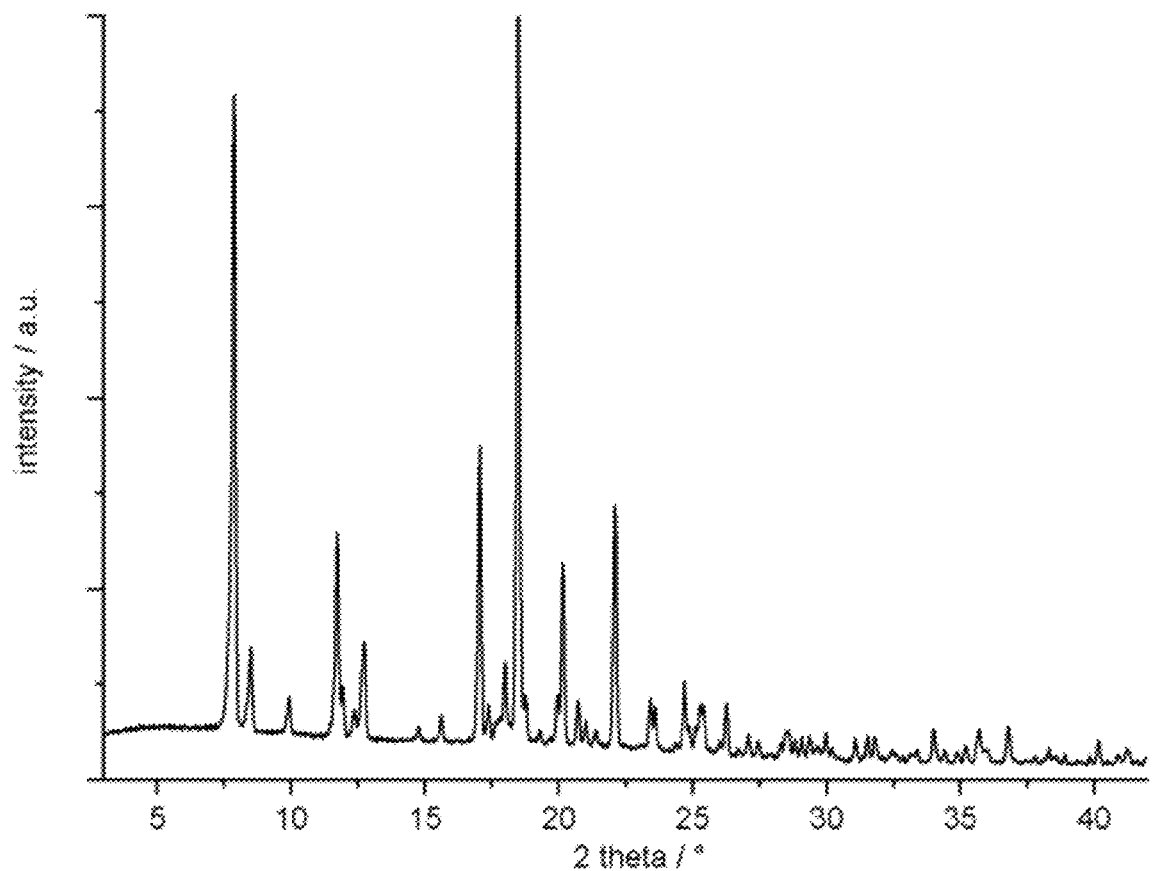
FIG. 3 illustrates a X-ray powder diffraction pattern of S-[2-([[1-(2-ethylbutyl)cyclohexyl]carbonyl]amino)phenyl] 2-methylpropanethioate crystalline form, also known as Form A.

Two tablets produced according to example 1 and example A were sliced and their X-ray pictures were collected. Both figures represent an overlayed of all X-ray slices that were generated during the measurement to reconstruct the 3D tablet. While FIG. 1 does not show any imperfection but a smooth surface, FIG. 2 has lot of cracks. These crack are also detectable by the human eye.

Example C

XRPD patterns of S-[2-([[1-(2-ethylbutyl)cyclohexyl]carbonyl]amino)phenyl] 2-methylpropanethioate crystalline form A were recorded at ambient conditions in transmission geometry with a STOE STADI P diffractometer (Cu K alpha radiation source, primary monochromator, position sensitive detector, angular range 3° to 42° 2 Theta, approximately 60 minutes total measurement time). The samples were prepared and analyzed without further processing (e.g. grinding or sieving) of the substance.

| 2theta/° | relative intensity/% |
|---|---|
| 7.9 | 86.3 |
| 8.5 | 16.2 |
| 11.7 | 30.7 |
| 12.7 | 17.1 |
| 17.1 | 41.6 |
| 18 | 14.6 |
| 18.5 | 100 |
| 20.2 | 27.2 |
| 22.1 | 33.7 |
| 24.7 | 11.9 |

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A composition, consisting of:
    a) 48% to 55% by weight of S-[2-([[1-(2-ethylbutyl)-cyclohexyl]-carbonyl]amino)phenyl]2-methylpropanethioate;
    b) 24% to 26% by weight of microcrystalline cellulose;
    c) 11% to 12% by weight of crospovidone micronized;
    d) 4% to 5% by weight of hydroxypropylmethyl cellulose;
    e) 4% to 6% by weight of croscarmellose sodium;
    f) 0 to 1% by weight of magnesium stearate;
    g) 0 to 1% by weight of colloidal silicon dioxide; and
    h) 0 to 1% by weight of sodium stearyl fumarate.

2. The composition according to claim 1, wherein the composition is in the form of a tablet.

3. The composition according to claim 1, wherein S-[2-([[1-(2-ethylbutyl)-cyclohexyl]-carbonyl]amino)phenyl]2-methylpropanethioate is in crystalline form.

* * * * *